(12) United States Patent
Bretthauer et al.

(10) Patent No.: US 9,877,725 B2
(45) Date of Patent: Jan. 30, 2018

(54) NEURAL PROSTHESIS AND METHOD FOR PRODUCING A NEURAL PROSTHESIS

(75) Inventors: Georg Bretthauer, Karlsruhe (DE); Selman Uranues, Graz (AT)

(73) Assignee: KARLSRUHER INSTITUT FUR TECHNOLOGIE, Karlsruhe (DE)

( * ) Notice: Subject to any disclaimer, the term of this patent is extended or adjusted under 35 U.S.C. 154(b) by 1020 days.

(21) Appl. No.: 13/515,211

(22) PCT Filed: Dec. 10, 2010

(86) PCT No.: PCT/EP2010/007536
§ 371 (c)(1),
(2), (4) Date: Nov. 19, 2012

(87) PCT Pub. No.: WO2011/069670
PCT Pub. Date: Jun. 16, 2011

(65) Prior Publication Data
US 2013/0060266 A1    Mar. 7, 2013

(30) Foreign Application Priority Data

Dec. 11, 2009  (DE) ........................ 10 2009 057 962

(51) Int. Cl.
*A61B 17/08*   (2006.01)
*A61B 17/11*   (2006.01)
*A61N 1/05*    (2006.01)
*A61N 1/36*    (2006.01)

(52) U.S. Cl.
CPC ........ *A61B 17/1128* (2013.01); *A61N 1/0551* (2013.01); *A61N 1/36103* (2013.01)

(58) Field of Classification Search
CPC .............. A61N 1/0551; A61N 1/36103; A61B 17/1128; A61B 2017/1132; A61B 17/11
See application file for complete search history.

(56) References Cited

U.S. PATENT DOCUMENTS 4,778,467 A  * 10/1988  Stensaas et al. ........... 623/23.64
5,656,605 A    8/1997  Hansson
6,090,117 A  *  7/2000  Shimizu ........................ 606/152
(Continued)

FOREIGN PATENT DOCUMENTS

DE   3323430     1/1985
DE   10053611    5/2002
(Continued)

OTHER PUBLICATIONS

International Search Report dated Aug. 4, 2011 issued in PCT Application No. PCT/EP2010/007536, 4 pages.

*Primary Examiner* — Gregory Anderson
*Assistant Examiner* — Sarah Simpson
(74) *Attorney, Agent, or Firm* — Harrity & Harrity, LLP (57) ABSTRACT

The invention relates to a neural prosthesis, a neural prosthesis for use in the treatment of severed nerves and to a method for producing a neural prosthesis. Said neural prosthesis comprises a coupling element receptacle and at least one coupling element having a first and a second coupling section, wherein the coupling element is fixed by the coupling element receptacle, and wherein the first coupling section can be arranged on a first nerve region and the second coupling section on a second nerve region so that both nerve regions can be coupled by means of the neural prosthesis.

19 Claims, 6 Drawing Sheets

(56) References Cited

U.S. PATENT DOCUMENTS

| | | | |
|---|---|---|---|
| 6,716,225 B2 | 4/2004 | Li et al. | |
| 7,147,647 B2 * | 12/2006 | Onyekaba | A61B 17/1128 606/152 |
| 2002/0161450 A1 * | 10/2002 | Doi | A61L 27/48 623/23.71 |
| 2008/0208300 A1 * | 8/2008 | Pasch | 607/116 |
| 2009/0024150 A1 | 1/2009 | Ahlers et al. | |
| 2009/0099597 A1 * | 4/2009 | Isse | 606/228 |
| 2010/0168870 A1 * | 7/2010 | Swain | A61B 17/11 623/23.72 |

FOREIGN PATENT DOCUMENTS

| | | | |
|---|---|---|---|
| WO | WO 97/37002 A1 | 10/1997 | |
| WO | WO 02/47557 A1 | 6/2002 | |

\* cited by examiner

NEURAL PROSTHESIS AND METHOD FOR PRODUCING A NEURAL PROSTHESIS

The subject matter of the application relates to a neural prosthesis, a neural prosthesis for the treatment of severed nerves, and to a method for producing a neural prosthesis.

In general, nervous tissue comprises nerve cells, dendrites, axons, and neuroglia. Nervous tissues can form nervous systems, the term nervous system comprising human or animal nervous systems.

Nerve cells (also referred to as neurons or nerve cell bodies) receive or trigger stimuli or impulses. Dendrites and axons transmit stimuli. Myelinated and unmyelinated axons are surrounded by neuroglia (glia cells) and mainly have a supporting, nourishing, and insulating function.

Generally speaking, a nerve cell (neuron) has one or more dendrites and usually one axon, which constitute a connection to other nerve cells to communicate with them. Dendrites serve as receivers of information. An axon, however, is responsible for transmitting information from one nerve cell to the other. In addition, a nerve cell body itself can also receive information and thus signals. An axon transmits information in the form of electric signals to synapses and thus to other nerve cells. Depending on the type of nerve cell, an axon can have a length of 1 µm to 1 m or more. The axons of the nerve cells of mammals have a thickness of about 0.5 to 10 µm.

The signals for transmitting information from or to a nerve cell are electric signals. In other words, the transmission of the electric signals is accomplished by nerve fibers. Due to the biomembrane of an axon, the outer wall of the axon exhibits a different electrical charge than an inner region of the axon. This difference in charge is also referred to as polarization or resting potential.

Irrespective of the class of a nerve cell, signal transmissions always consist of changes in the electric potential over a plasma membrane of a nerve cell or neuron. Changes, which are also waves of electrical excitation, are also referred to as action potential or nerve impulses.

In particular, in the following, nerve cells can be all classes of nerve cells, i.e. for example unipolar nerve cells, bipolar nerve cells, pseudounipolar nerve cells, and multipolar nerve cells.

In the following, the term nerve will mean a nerve cell and in particular a nerve fiber. In particular, the term nerve will also mean a part or section of a nerve cell. Moreover, in the following, the term nerve area will mean a portion, part, or area of a nerve cell or a nerve.

If the nerve fibers for signal transmission are interrupted, information cannot be transmitted from or to a sensory cell. Thereby, the function of the respective sensory cell, e.g. an organ, a skin area or a muscle, is disturbed. For example, numbness can be the result, and sensations cannot be perceived consciously any more. Likewise, nerve cells of the spinal cord or the brain can no longer transmit information for controlling muscles and glands, so that affected muscles and glands remain inactive.

For example, in the case of paraplegia, the signal transmission of nerves or nerve fibers running through the spinal cord is interrupted. That is why in the case of paraplegia both the sensation from the cut off sensory cells and the activity and fluid production of muscles and glands of the affected area is missing.

In other words, if nerves are severed or injured, nerve signals are partially or even fully interrupted. As a result of the disturbance of nerve signals, degeneration of the affected nerves is caused. As a consequence, the normal physical activity and further bodily functions of affected living beings, such as humans or animals, are strongly affected here. It is particularly problematic that severed or injured nerves usually necrotize before their growing together can be accomplished. Thus, a permanent interruption of nerve signals can arise before a normal and unaffected transmission of nerve signals is restored by growing together.

It is an object of the present invention to restore a transmission of nerve signals in the case of injured or severed nerve fibers.

According to the invention, this object is solved by the features of the independent claims. Preferred embodiments of the invention are subject of the dependent claims.

Neural Prosthesis According to One Aspect

An aspect of the present invention relates to a neural prosthesis, comprising:
a coupling element receptacle, and
at least one coupling element having a first and a second coupling portion, wherein
the coupling element is secured by the coupling element receptacle, and wherein
the first coupling portion is arrangeable at a first nerve area and the second coupling portion is arrangeable at a second nerve area, so that the two nerve areas are coupleable by means of the neural prosthesis.

Advantageously, the neural prosthesis enables nerve regeneration and prevents muscular atrophy, also referred to as muscular deformation or tissue atrophy. Further advantageously, the neural prosthesis accelerates the body's own reparation processes and restores the signal transmission via the injured nerve region.

In particular, a neural prosthesis means an intermediate piece that can be inserted between proximal and distal ends of a nerve or nerve fiber. A connection between two separated nerve areas or ends of a nerve can be established by means of a neural prosthesis. In other words, a neural prosthesis serves as a connector of a first nerve area with a second nerve area. In particular, a first and a second nerve area mean a distal and a proximal nerve end or area, respectively. The two nerve areas can form due to a nerve being severed, for example. The two nerve areas can be opposite to each other starting from a point of severing.

Embodiments of the Neural Prosthesis

The neural prosthesis comprises at least one coupling element receptacle that forms a basic or base body. Advantageously, the configuration, i.e. the structural design, of the base body or coupling element receptacle is adapted to specific fields of application in a human or animal body. Accordingly, the geometric configuration or dimensioning of coupling element receptacles can differ depending on the field of application or body region of use. For example, a coupling element receptacle can have a substantially round, oval, or flat, elongated configuration. For example, the coupling element receptacle can have a substantially circular or oval or rectangular cross-section, for example. This applies particularly to a cross-section in a sectional plane perpendicular to a longitudinal axis of the coupling element receptacle. Moreover, neural prostheses can be configured substantially symmetrically as well as asymmetrically.

In particular, a coupling element receptacle can comprise at least one first and one second contact area, wherein the first and the second contact area are arrangeable at a first and a second nerve area, respectively. Preferably, the first contact area contacts a first nerve area, e.g. a proximal nerve area. Preferably, the second contact area contacts a second nerve area, e.g. a distal nerve area. Preferably, the first and the second coupling portion of a coupling element can be arranged at a respective contact area of the coupling element receptacle.

Preferably, the coupling element receptacle comprises at least one coupling element having a first and a second coupling portion. Further preferably, the at least one coupling element is secured by the coupling element receptacle.

The term secured in particular means that the coupling element is held or fixed by the coupling element receptacle. In particular, an alignment of the coupling element with respect to the coupling element receptacle is definable or determinable by the coupling element receptacle. For example, the coupling element and the coupling element receptacle can form a chemical and/or mechanical bond. A chemical bond can be accomplished by gluing, for example. A mechanical bond can be accomplished by a friction fit, for example.

An alignment of a coupling element relative to a coupling element receptacle is determined preferably before the insertion of a neural prosthesis between a distal and a proximal nerve end. Preferably, a coupling element is arranged at or secured by a coupling element receptacle such that a first coupling portion is arranged in the first contact area of the coupling element receptacle and a second coupling portion is arranged in the second contact area of the coupling element receptacle.

The first coupling portion and the second coupling portion of the coupling element are arrangeable at a first and a second nerve area, respectively.

In particular, the terminology that a coupling portion is arrangeable at a nerve area also means that a coupling portion of a coupling element can be brought into contact or engagement with a nerve area, respectively. In particular, a coupling portion is arrangeable at a nerve area such that a coupling portion and a nerve area only contact each other or are tangent to each other, respectively.

In a further configuration, a coupling portion and a nerve area can be arranged at each other such that a coupling portion is surrounded or enclosed by a nerve area, respectively. In this case, the coupling portion can be arranged by being inserted or stuck into the tissue of a nerve area. Further preferably, a nerve area can be surrounded or enclosed by a coupling portion. Here, the coupling portion can be placed onto a nerve area like a shell or cap, or cover a nerve area.

Further preferably, a coupling element and a respective nerve area can be fixed to each other. In particular, fixation can be accomplished by stitching or gluing together. Moreover, fixation can be achieved by clamping tissue of the nerve area and the coupling element together. Also, fixation or retention can be achieved by hooking the coupling element in tissue of the nerve area.

Thus, preferably, the first coupling portion is arrangeable at a first nerve area and the second coupling portion is arrangeable at a second nerve area, so that the two nerve areas are coupleable by means of the neural prosthesis.

Further preferably, the neural prosthesis can comprise more than one coupling element. The number of coupling elements may depend on the body region to be treated or on the living being to be treated. In particular, 2 to 6, preferably 3 coupling elements can be used for treatment in the human body. A higher number of coupling elements for the use of a neural prosthesis in the human body is possible though. For example, 4, 5, 6, 7, 8, 9, 10, 15, 20 etc. coupling elements can be present. In particular with animals, the number of coupling elements to be used can vary depending on the type of animal and the body region or nerve to be treated.

Preferably, a neural prosthesis can comprise a coupling element receptacle including a plurality of tubular conducting elements. In particular, the conducting elements can be configured as microtubes.

In addition, the conducting elements can extend in a longitudinal direction in the coupling element receptacle, wherein the longitudinal direction is a direction substantially parallel to the at least one coupling element. Moreover, a longitudinal direction can mean a direction that is substantially perpendicular to one or both of the contact areas of the coupling element receptacle. In other words, a longitudinal direction can be a direction parallel to a coupling axis, which is aligned substantially normal to the contact areas. Preferably, the coupling axis is arranged in the center of or centrally in a neural prosthesis. The coupling axis may correspond to a line of symmetry of a neural prosthesis.

Preferably, the tubular conducting elements are configured as hollow cylinders. In other words, a conducting element advantageously has at least one passage.

In particular, a tubular conducting element can be a conducting element that has at least one passageway, one feedthrough, one channel, one passage, or one possibility for the passing of fluids. In other words, a tubular conducting element has a hollow area.

It is to be understood that a geometric configuration of a tubular conducting element can be varied. For example, the tubular conducting element can have an oval or polygonal passage. Moreover, a tubular conducting element can have more than one passage, wherein the passages do not have to have the same dimensions. Preferably, a passage or fluid channel of a tubular conducting element extends from the first contact area to the second contact area of the coupling element receptacle. In particular, the dimensions of the passages may depend on the specific body region to be treated.

Furthermore, the dimensions of the passages of a plurality of tubular conducting elements of a coupling element receptacle can vary. Therefore, tubular conducting elements of a coupling element receptacle having a passage with a larger dimension can preferably be arranged in the marginal or outer area of the coupling element receptacle, for example. In another embodiment, tubular conducting elements of a coupling element receptacle having a passage with a smaller dimension can preferably be arranged in the marginal or outer area of the coupling element receptacle. Likewise, tubular conducting elements having a passage with a larger and a smaller dimension can be arranged in a central area and also in a marginal area of a coupling element receptacle.

In particular, a tubular conducting element can be configured such that tissue of a nerve area can grow through the tubular conducting element. Further preferably, a conducting element permits the migration of components, such as blood, growth hormones, cells from the first nerve area to the second nerve area. In other words, a tubular conducting element permits the passage of fluids.

Further preferably, a tubular conducting element can comprise an elastic or resilient material, so that damage of tissue or cell material adjoining the nerve or of the nerve itself can be avoided. In particular, one or more tubular conducting elements can fully be made of the elastic or resilient material.

Further preferably, the coupling element receptacle comprises or includes one or more rod-shaped conducting elements. Rod-shaped conducting elements particularly do not have a passage or fluid channel. Just like the tubular conducting elements, the rod-shaped conducting elements can be arranged in a coupling element receptacle according to a specific structuring (distribution). Preferably, the rod-shaped conducting elements extend analogously to the tubular conducting elements in the longitudinal direction of the coupling element receptacle.

Also, the outer geometry of a tubular or rod-shaped conducting element can have a varied configuration. For example, a tubular and a rod-shaped conducting element can have the outer form of a cubuid, a truncated cone, or a prism. In particular, the geometry of a tubular or rod-shaped conducting element can determine its mechanical properties with respect to bending, torsional, compressive and tensile loads such that these properties are optimized for the respective use or the respective application. In particular, a plurality of tubular and/or rod-shaped conducting elements of a coupling element receptacle can have mutually different geometric configurations.

Further preferably, a bundle or a plurality of tubular and/or rod-shaped conducting elements form or forms the coupling element receptacle. In particular, the tubular and/or rod-shaped conducting elements can be arranged substantially loosely at each other and be fixed to each other by a form and/or friction and/or force fit, such as by a retaining strap. Moreover, the tubular and/or rod-shaped conducting elements can be fixed to each other substantially by bonding, such as by melting or gluing.

Further preferably, in a tubular conducting element that compared to other rod-shaped and/or tubular conducting elements of the same coupling element receptacle has a larger dimension, in particular a larger diameter, rod-shaped and/or tubular conducting elements having a relatively smaller dimension, in particular a relatively smaller diameter, can be arrangeable in the passage of the larger conducting element. In other words, the inner diameter of the larger conducting element can be equal to or larger than the outer diameter of the smaller conducting element.

Further preferably, at least one of the tubular and/or rod-shaped conducting elements of a coupling element receptacle is formed as a stabilizing element. In particular, a stabilizing element has a higher strength than other conducting elements, so that each stabilizing conducting element compared to a tubular and/or rod-shaped conducting element, which in this context can also be referred to as a non-stabilizing conducting element, can be bent less easily.

For example, a tubular and/or rod-shaped conducting element that is formed as a stabilizing element can comprise a metallic material, whereas conducting elements having less strength include gelatin. Further preferably, a stabilizing element can comprise gelatin as the material thereof, which has a longer molecular chain than other tubular and/or rod-shaped conducting elements having lower strength. It is also possible that all conducting elements are formed of an identical material, the stabilizing conducting elements being formed more compact though, e.g. by being formed as a solid or massive body, i.e. hollow body-free.

Further preferably, the at least one coupling element is arranged in the coupling element receptacle, wherein the first and the second coupling portion project beyond a first and a second contact area of the coupling element receptacle, respectively.

Preferably, the at least one coupling element is arranged in or next to a conducting element.

Preferably, the coupling portions project about 0.1 µm to about 8 mm or about 5 mm to 3 cm out from the contact area of the coupling element receptacle. In other words, the coupling portions can have a length of about 1 µm or more. Further preferably, the coupling portions have a width of about 0.1 µm to 3 mm.

Further preferably, each coupling element has at least two coupling portions. In other words, the at least 2 coupling portions are arranged substantially opposite or opposed to each other. The ends of the coupling portions are either acute or obtuse. Particularly preferably, each coupling element has 3, 4, 5, 6 etc. coupling portions. In other words, a coupling element with more than 2 coupling portions or several ends at a coupling portion has a bifurcated branching.

In particular, in this context, the term acute means that one end of a coupling portion has a taper or decreasing gradation or stepping toward the end and/or at least one acute angle. In particular, a cone or pyramid-shaped as well as a syringe or injection needle-shaped end can be considered to be acute.

On the other hand, the term obtuse in this context means a rather flat, rounded, or only slightly tapered end of a coupling portion. In particular, the terminology "acute or obtuse end of the coupling element" includes the configuration of a body edge and/or a wall area or surface of an end of a coupling portion. For example, an acute end can be sharp-edged and/or have sharp-cutting properties. In particular, a cutting plane, which extends along an acute or obtuse end, is arranged at a substantially acute or obtuse angle with respect to the coupling axis of a neural prosthesis.

Further preferably, the at least one coupling element is hollow. In other words, the coupling element comprises at least one fluid channel, which constitutes a connecting channel between the two ends of the coupling element and thus between the first and second coupling portions.

Preferably, the coupling element has a tubular configuration. It is preferred for a coupling element to be configured as a hollow cylinder or as a tubular element. Further preferably, a coupling portion can be formed similar to or like a syringe or injection needle, in particular similar to or like an end area of a syringe or injection needle.

For example, in one configuration of a coupling portion the coupling portion can have a width such that an axon, which is arranged within a nerve area, is arranged substantially within the hollow cylinder. Further preferably, a coupling portion has a width such that a nerve fiber or an axon is arranged at least partially within the hollow cylinder of the coupling portion.

In a further configuration, at least one coupling portion can have one or more recesses in a circumferential surface/lateral area or wall of a hollow-cylindrical coupling portion. Such a recess constitutes an inlet and/or outlet, which additionally or alternatively permits the arrangement or insertion of at least part of a nerve area within the hollow cylinder of the coupling portion.

Preferably, coupling elements can have at least one coupling portion having a hollow-cylindrical end with a passage, and a coupling portion having at least one passage exclusively in the wall of the coupling portion.

Moreover, a neural prosthesis can include several coupling elements with differently configured coupling portions.

Further preferably, the at least one coupling element has at least one branching, from which at least one third coupling portion branches off.

Particularly preferably, with a coupling element including first through third coupling portions, two coupling portions project beyond a first contact area and a third coupling portion projects beyond a second contact area. In other words, a coupling element can have a bifurcated shape. Moreover, a coupling element can include more than one branching, so that e.g. at least two coupling portions project beyond each contact area of a coupling element receptacle, so that a coupling element has at least four coupling portions.

Further preferably, a coupling element receptacle can have more than two contact areas. For example, a coupling element receptacle can have three contact areas, wherein one coupling portion of a coupling element projects beyond each contact area.

Advantageously, coupling elements allow a targeted growing together of nerve areas and allow a contact between the severed nerve tracts or areas.

Further preferably, a neural prosthesis comprises a jacket. In a preferred embodiment, the coupling element receptacle and at least partially the at least one coupling element are arranged within the jacket.

In one configuration, a coupling portion can project farther beyond a contact area or a coupling element receptacle than an area of a jacket projects beyond the coupling element receptacle, and vice versa.

Preferably, the jacket stabilizes the coupling element receptacle with respect to destructive mechanical action. In the arrangement state, the jacket can in particular protect an arranged nerve, particularly the nerve areas arranged in the coupling portions. Furthermore, the connection between the nerve areas and the coupling portions can be protected and stabilized as well. In addition, the jacket can also protect the coupling elements against the action of forces. Moreover, the jacket can include a material that stabilizes the coupling element receptacle and the at least one coupling element against chemical action.

Preferably, the jacket is substantially a hollow cylinder. In other words, the contact areas and the coupling portions can be left free from the jacket or do not have to be covered with the jacket.

In particular, the jacket projects beyond the coupling element receptacle preferably from about 0.1 μm to about 8 mm. Further preferably, the jacket projects beyond the coupling element receptacle from about 0.2 μm to about 20 mm, particularly preferably between about 2 mm to about 15 mm. Stated differently, the jacket extends in the longitudinal direction from the coupling element receptacle toward the ends of the coupling elements.

Further preferably, the areas of the jacket surround the first and second contact areas of the coupling element receptacle. Preferably, these areas of the jacket define a first and a second adaptation area each. Preferably, the respective adaptation area has a width of about 0.5 μm to about 2.8 mm, or from about 2.5 mm to about 10 mm, or from about 2.3 mm to about 15 mm.

Preferably, the width of the respective adaptation area is equal to or greater than the width of the respective nerve area.

Advantageously, the jacket, which can also be defined as a cover, serves to join separated nerve ends or areas together in a stable way and permits easy handling during surgery or surgical procedures for insertion of the neural prosthesis.

In a further configuration, the neural prosthesis is configured as an integral element. Here, the neural prosthesis comprises one or more channels. Coupling elements can at least partially be arranged in the channels. The configuration and functionality of the channels can be similar to the tubular conducting elements. Accordingly, it is possible, for example, that the channels permit a migration of bodily components, such as hormones, blood cells, etc.

Preferably, a neural prosthesis includes three or more coupling elements. The three or more coupling elements can be secured by corresponding channels.

Preferably, at least one rod-shaped conducting element can be arranged in a channel. Moreover, a stabilizing element can be arranged in a channel.

Further preferably, the jacket and the coupling element receptacle include resorbing material. Thereby, after an average expected or predefined or predetermined healing duration, it can be ensured that the neural prosthesis is substantially absorbed after an absorption period. Advantageously, by absorption of components of a neural prosthesis, it can be ensured that the body tissues can spread in a treated body region in an unhindered way and in full. Thus, in the long term, after treatment of severed nerves, the original ambient conditions of the healed nerve material and of the tissue surrounding the nerve can substantially be restored. Thus, the term resorbed in particular includes that the resorbed material is dissolved. Hence, the jacket and the coupling element receptacle can be dissolved, i.e. decomposed by the body, substantially fully after absorption.

Advantageously, the neural prosthesis comprises resorbing materials having mutually different absorption times. In particular, due to different absorption times of different areas or elements of the neural prosthesis, healing conditions of a severed nerve can be controlled for the duration of the healing process.

For example, it can be advantageous that at least a plurality of the conducting elements of the coupling element receptacle has a shorter absorption period than the jacket. Thus, the conducting elements can already be partially absorbed during a healing process, so that the nerve and/or the tissue surrounding the nerve can grow or regenerate in an unhindered way, while the jacket has not yet or only initially been absorbed. Hence, the jacket can still have sufficient stability against outside influences, which might disturb the nerve growth or damage the nerve.

Moreover, at least one of the conducting elements is formed as a stabilizing element, which has a higher absorption resistance than other conducting elements.

Preferably, the resorbing material is gelatin and/or polyglycolic acid.

Further preferably, the at least one coupling element is at least partially made of non-resorbable material. Preferably, the non-resorbable material is a metal. In particular, titanium can be used as the non-resorbable material. Further preferably, metals or metal alloys are used, which have anergic and/or anti-allergenic properties. In particular, surgical steels or medical materials or metals can be used.

If a coupling element includes both resorbable and non-resorbable material, the resorbable material is preferably gelatin.

Advantageously, the absorption time of the resorbing material can be determined by the length of the molecular chain.

Further preferably, the neural prosthesis is substantially absorbed after an absorption period of 9 months. Depending on the body region to be treated, the absorption time can be determined such that the neural prosthesis is resorbed substantially after 3 months, after 6 months, or only after a period between 12 and 24 months.

Particularly preferably, the neural prosthesis is substantially bioresorbable. Further preferably, the neural prosthesis is substantially biocompatible.

The neural prosthesis can comprise one or more stimulators, even though the functional performance of the above-described neural prosthesis is also given without a stimulator. In other words, the neural prosthesis is substantially free of stimulators. In particular, the neural prosthesis is completely free of stimulators.

Preferably, the neural prosthesis can comprise at least one biochemical stimulator. The biochemical stimulator can be adapted to stimulate coupling of the two nerve areas. Preferably, the at least one stimulator is arranged in one or more of the conducting elements and/or in one or more of the channels. Additionally or alternatively, one or more biochemical stimulators can be arranged in the at least one coupling element. In particular, the term stimulator means activators that prevent formation of unfavorable healing conditions and/or that improve the healing conditions.

Preferably, the stimulators are released at least at the beginning of the absorption period via the contact areas of the coupling element receptacle.

Further preferably, mechanical and/electrical stimulators are arrangeable at the neural prosthesis.

Nerve stimulators are devices that generate electric current via a depolarization at nerves. The current strength and the current frequency (frequency) can vary as required. The stimulation width (duration of the individual stimulation pulses) can also vary in length. Also, the nerve fibers to be stimulated can be selectively sensory or motor fibers. Stimulation current devices can also be used for this purpose.

In other words, electrical stimulators (nerve stimulators) can be devices, components, and in particular microelectronic and/or electromechanical component parts that generate electric current via a depolarization at nerves. The current strength and the frequency of the electrical stimulators can be different depending on the specific application or body region and living being (human, specific animal species) to be treated. The stimulation width of the devices, which means the duration of the individual stimulation pulses, can also be variably adjustable. If an electrical stimulator is applied in a body or nerve to be treated, the stimulation can be made up of different stimulation widths, for example alternating stimulation widths. Moreover, the nerve fibers to be stimulated can be sensory or motor fibers. Furthermore, stimulation current devices can be used to stimulate nerve fibers.

Further preferably, special stimulators can be employed depending on the application case. Preferably, universal stimulators are used.

For example, mechanical and/or electrical stimulators can be arranged at the jacket of the neural prosthesis. In addition, mechanical and/or electrical stimulators can be arranged at a neural prosthesis via coupling elements, in particular coupling portions.

Further preferably, at least one surgical suture is arranged at a neural prosthesis. The at least one surgical suture enables or permits coupling of at least one nerve area to the neural prosthesis.

Preferably, a surgical suture is arranged in the coupling element receptacle. Further preferably, a surgical suture can be passed through the coupling element receptacle.

Preferably, a surgical suture is arranged in a tubular conducting element. For example, a surgical suture is inserted into a tubular conducting element, wherein at least one suture end projects out of at least one of the contact areas.

Further preferably, a surgical suture is fixed or fastened to a neural prosthesis.

Neural Prosthesis for Use According to One Aspect

One aspect of the invention comprises a neural prosthesis to be used in the treatment of severed nerves.

Preferably, one or more elements or features of the neural prosthesis to be used in the treatment of severed nerves can comprise one or more embodiments or configurations of the above-described neural prosthesis.

Method According to One Aspect

One aspect of the invention comprises a method for producing a neural prosthesis, comprising the steps of:
providing a plurality of conducting elements; and
arranging at least one coupling element at the plurality of conducting elements;
wherein the plurality of conducting elements forms a coupling element receptacle, and wherein the coupling element is secured by means of the coupling element receptacle.

One or more coupling elements can respectively be arranged in a conducting element.

Variants of the Method

Preferably, the at least one coupling element is at least partially fixed to the coupling element receptacle by pressing, melting, or gluing.

Preferably, the method also comprises the further step of arranging a jacket.

Preferably, the jacket is at least partially fixed to the coupling element receptacle by pressing, melting, or gluing.

Preferably, the coupling element receptacle, the at least one coupling element, and the jacket are at least partially fixed to each other by pressing, melting, or gluing.

Preferably, the method for producing a neural prosthesis can comprise one or more aspects relating to use or configuration of the neural prosthesis.

Advantageously, the neural prosthesis described in this application can be inserted into a damaged nerve tissue or damaged nerve for bridging nerve signals without further auxiliaries or additional devices. Thus, the neural prosthesis is suitable for easily and quickly restoring a disturbed nervous activity. In particular, only little time is required for the insertion of such a neural prosthesis into damaged tissue. Moreover, no special apparatuses or a special surgical environment is required, which makes a broad application range of the neural prosthesis possible.

In addition, such a neural prosthesis can be produced and used in a simple and cost-effective manner. Thereby, costs occurring for the treatment and care of persons having damaged nerves can be reduced and healing of a person can be achieved at low costs.

In particular, by inserting the neural prosthesis into damaged tissue, the transmission of nerve pulses, nerve regeneration, and muscle contraction can be achieved.

Advantageously, traumatic nerve lesions and resulting degenerative states, such as in stroke patients, can be treated in a targeted manner by using a neural prosthesis. Furthermore, in addition to peripheral nerve lesions, spinal cord lesions can be treated as well.

It is particularly advantageous that the neural prosthesis is resorbable, easy to handle, tissue-conserving or smooth, and can be manufactured industrially.

Further preferably, the neural prosthesis can be produced with different dimensions to achieve the best possible adaptation at the location of use.

It is particularly advantageous that the neural prosthesis can be configured as a finished product, which can easily be stored in any operating room without any further measures and can be used immediately if required. Thereby, one of the most important prerequisites for a restitutio ad integrum, the quickest possible bridging of the defect area at the nerve, can be met. Shortly after a nerve has been severed, trauma-induced tissue reactions at the nerve (such as edema, hematoma, inflammation) exist only to a small extent and the atrophic reactions can be prevented at a so-called effector organ or sensory cell (such as the muscular system). A delayed nerve function, however, would result in a lengthy process of muscle growth in the tend area of the nerve.

Further, it is advantageous that the neural prosthesis is dissolved by way of absorption after completion of the regeneration of the respective nerves. For example, only one or more coupling elements remain, which serve as existing electrodes in the nervous tissue. These electrodes (such as coupling elements of titanium) are anergic and elements that do not disturb nerve function. In addition, it is advantageous that such coupling elements lead to increased tissue stability in a formerly injured zone or treated body region, whereby better protection against outside influences (as is possible if bone injuries are present at the same time) is ensured.

SHORT DESCRIPTION OF THE FIGURES

The invention will be described by way of example in the following on the basis of embodiments with reference to the accompanying drawings, the general concept of the invention not being limited to the embodiments. In particular, individual features of the above and/or below-described aspects and/or embodiments can be combined to form further embodiments separately from the respective aspect and/or embodiment.

The figures show.

DETAILED DESCRIPTION OF THE FIGURES

In particular, in the following, nerve cells can be all classes of nerve cells, i.e. for example unipolar nerve cells, bipolar nerve cells, pseudounipolar nerve cells, and multipolar nerve cells.

In the following, the term nerve will mean a nerve cell and in particular a nerve fiber. In particular, the term nerve will also mean a part or section of a nerve cell. Moreover, in the following, the term nerve area will mean a portion, part, or area of a nerve cell or a nerve.

Figure 1:
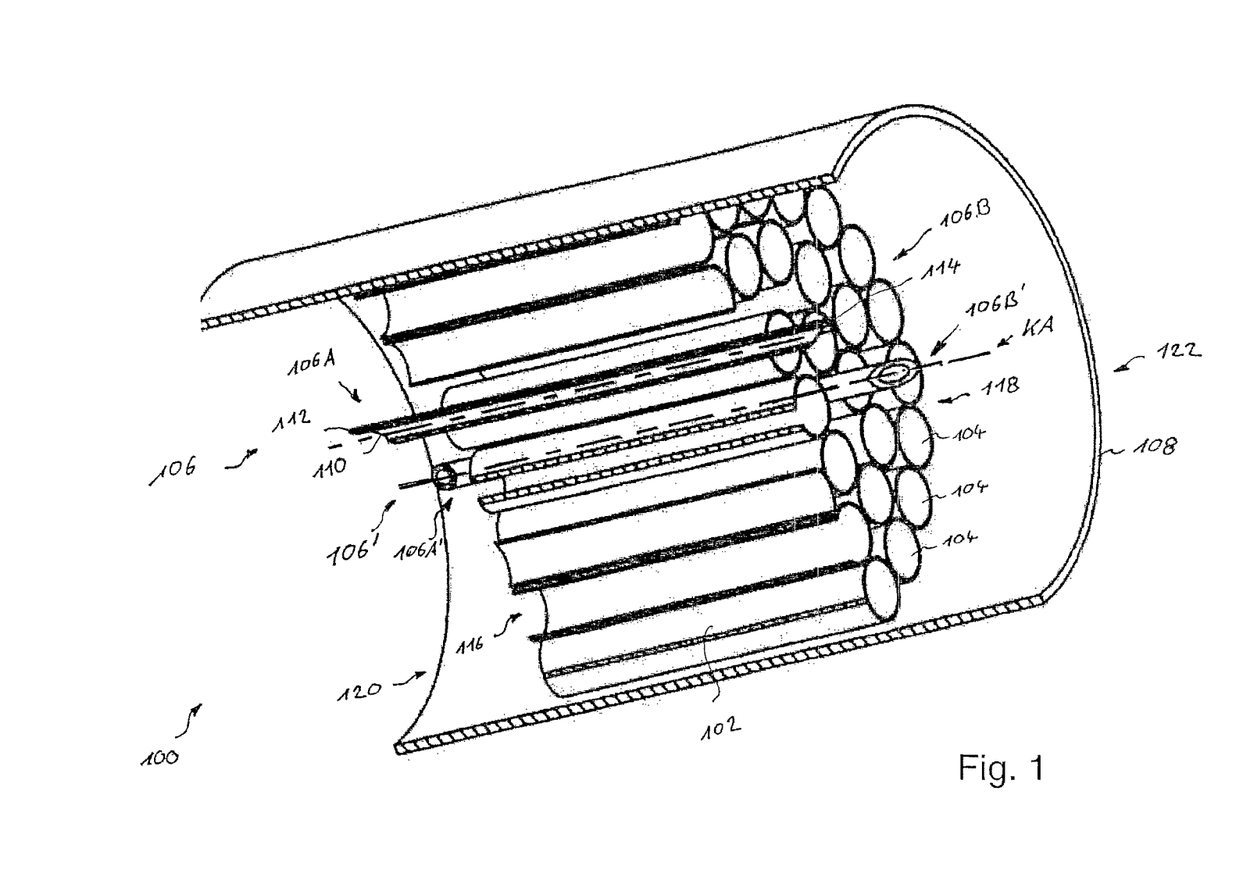
FIG. 1: a perspective representation of a neural prosthesis.

FIG. 1 shows a perspective representation of a neural prosthesis 100 having a coupling element receptacle 102, which comprises a plurality of conducting elements 104, two coupling elements 106, 106', and a jacket 108.

Each of the two coupling elements 106, 106' has a first coupling portion 106A, 106A' and a second coupling portion 106B, 106B', wherein the two coupling elements being secured by the coupling element receptacle 102. The two coupling elements 106, 106' are arrangeable at two nerve areas (not shown) each.

For example, the respective first coupling portions 106A, 106A' can be arranged at a first nerve area and the respective second coupling portions 106B, 106B' can be arranged at a second nerve area when the neural prosthesis 100 was inserted into a human body to be treated to couple mutually separated nerve areas. For example, after insertion of the neural prosthesis 100, a first coupling portion 106 can be coupled to a first nerve area, which corresponds to a distal nerve end, whereas a second coupling portion 106B is coupled to a second nerve area, which corresponds to a proximal nerve end.

As can be seen from FIG. 1, the conducting elements 104 are substantially tubular, which is why the conducting elements can be referred to as tubular conducting elements. Moreover, the conducting elements 104 are arranged substantially in parallel to each other and are aligned substantially in parallel along a longitudinal direction of the neural prosthesis 100.

The coupling element receptacle 102 is substantially formed by the conducting elements 104. The conducting elements can approximately have the same or similar dimensions in the longitudinal direction or coupling direction KA. The coupling direction KA and the longitudinal direction are preferably parallel. Also, as is shown, the dimensions transversely to the coupling direction KA can be the same or similar. In other words, the diameter of the conducting elements can be similar.

In a modified embodiment of the neural prosthesis 100, the conducting elements 104 are dimensioned differently from each other in a transverse and/or longitudinal direction. Furthermore, the conducting elements can have a geometry (such as truncated cone or prism) different from a hollow-cylindrical configuration. In particular, the mechanical properties of the conducting elements can be controlled by the dimensions and geometries thereof, so that the individual conducting elements and in particular the coupling element receptacle comprising a plurality of conducting elements have matched mechanical properties with respect to a specific application case or a body region to be treated.

In this embodiment of a neural prosthesis, the longitudinal direction corresponds to a line of symmetry of the neural prosthesis and a coupling axis KA.

Furthermore, the neural prosthesis 100 comprises two contact areas 116, 118, which preferably extend substantially perpendicular to the coupling axis KA. In other words, the contact areas 116, 118 are formed by the respective ends of the conducting elements 104.

The contact areas 116, 118 can be formed as planes, as is shown in FIG. 1. In another embodiment, the contact areas can be uneven surfaces having projections or recesses. In particular, the term projection or recess in this context means that one or more conducting elements, compared to other conducting elements, project beyond or are offset backward from other conducting elements in the longitudinal direction.

If nerve areas are coupled to the neural prosthesis 100, this is usually done in the longitudinal direction or along the coupling axis KA. Preferably, coupled nerve areas can contact or be tangent to the respective contact area.

Also, in the illustrated embodiment of the neural prosthesis 100, the two coupling elements 106, 106' are arranged in parallel to the coupling axis KA.

In a modified embodiment of the illustrated neural prosthesis 100, it is also possible that the coupling elements 106, 106' are not arranged in parallel, but at a set or determined angle with respect to the coupling axis KA. Likewise, the conducting elements 104 or at least some of the conducting elements 104 can enclose an angle with the coupling axis KA.

As is shown in FIG. 1, the coupling elements 106, 106' can be formed substantially as hollow cylinders, so that the coupling elements have a passage or fluid channel. For example, the coupling element 106 comprises a passage 110, which extends from a first end 112 of the coupling element 106 to a second end 114 of the coupling element 106.

According to FIG. 1, the ends 112, 114 of a coupling element or coupling portion 106A, 106B can be formed acutely. This means in particular that a sectional plane, which e.g. extends along an end 112, intersects the coupling axis KA substantially at an acute angle.

According to a further embodiment, at least one end of a coupling element can have a sectional plane that extends substantially normal to the coupling axis KA.

In particular, the coupling portions 106A-B' project out of the coupling element receptacle 102, as is shown in FIG. 1.

Furthermore, it is also possible that a coupling portion constitutes a local elevation or local protrusion.

In particular, depending on the dimensions of a coupling portion and/or neural prosthesis, the coupling portions can project out from the contact area of the coupling element receptacle by about 0.1 μm to 5 μm, about 3 μm to about 30 μm, about 25 μm to about 1 mm, about 1 mm to about 8 mm, and/or about 5 mm to about 3 cm.

The neural prosthesis 100 further comprises a jacket 108 that substantially surrounds or encloses the coupling element receptacle 102. In other words, the coupling element receptacle 102 and at least partially the coupling elements 106, 106' are arranged within the jacket.

The jacket 108 illustrated in FIG. 1 is substantially a hollow cylinder. Depending on the configuration of a neural prosthesis 100, the jacket 108 can project beyond the contact areas 116, 118 of the coupling element receptacle 102 by about 0.1 μm to about 50 μm, about 30 μm to about 3 mm and/or 2 mm to 8 mm or more.

Moreover, a jacket can be configured such that it only surrounds the coupling element receptacle or at least one of the coupling portions.

As is illustrated in FIG. 1, the areas of the jacket 108, which project beyond the coupling element receptacle 102, can surround the first and second contact areas 116, 118 and respectively define a first adaptation area 120 and a second adaptation area 122.

For example, the respective adaptation area 120, 122 can have a width from about 0.2 μm to about 20 mm, preferably from about 0.5 μm to about 2.8 mm, or from about 2.5 mm to about 10 mm. Furthermore, the respective adaptation area 120, 122 can have a width from about 2.3 mm to about 15 mm, for example.

In particular, an adaptation area can receive a nerve area. In particular, a nerve area can be supported or fixed or held by an adaptation area. Moreover, a nerve area can substantially be protected from outside influences by an adaptation area.

The conducting elements 104, which the coupling element receptacle 102 comprises, are secured or fixed by the jacket 108. The coupling elements 106, 106' are also secured by the jacket 108. For example, the conducting elements 104 and the coupling elements 106, 106' can be secured in their arrangement by a force-fit connection with the jacket 108.

In a modified configuration, the conducting elements 104 can be connected to each other by bonding or by a form fit. The jacket 108 can also be connected to the coupling element receptacle 102 by bonding or by a form fit. Alternatively, the jacket 108 is connected to the coupling element receptacle 102 by a force fit, whereas the conducting elements 104 are connected to each other by bonding.

In at least one of the conducting elements 104 and/or in the coupling elements 106, 106' there can be arranged stimulators (not shown), which promote or foster wound healing or nerve growth.

Preferably, bonding can be accomplished by means of gelatin as an adhesive.

Figure 2:
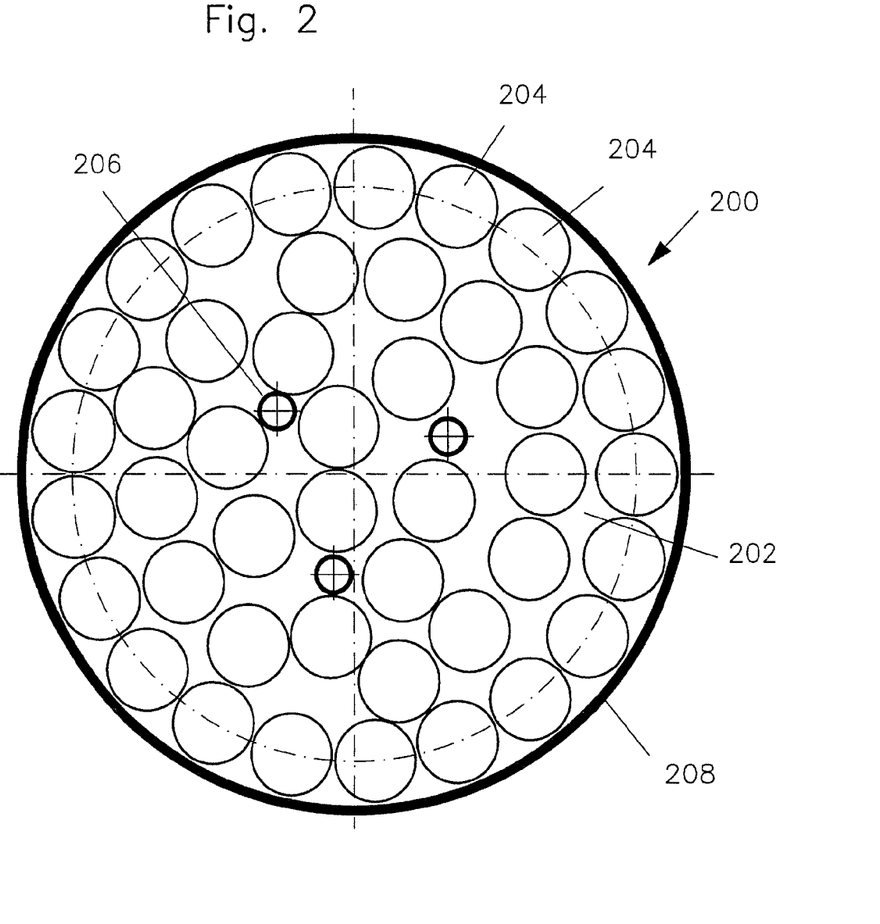
FIG. 2: a schematic representation of a portion of a neural prosthesis in section along a transverse direction.

FIG. 2 exemplarily shows a schematic representation of a portion of a neural prosthesis 200, which comprises a multitude/plurality of conducting elements 204 forming a coupling element receptacle 202, three coupling elements 206, and a jacket 208. In particular, FIG. 2 can be a sectional view of FIG. 1, so that the neural prosthesis 100 and the neural prosthesis 200 can be identical, the conducting elements 104 and the conducting elements 204 can be identical, the coupling elements 106, 106' and the coupling elements 206 can be identical, and the jacket 108 and the jacket 208 can be identical.

It can be taken from FIG. 2 that the conducting elements 204 can be arranged at each other partly without any specific or apparent rule. Another part (the outer row of the conducting elements 204) is arranged on a line of symmetry though.

The coupling elements 206 are arranged next to conducting elements 204. In a modified embodiment, at least one of the coupling elements 206 could be arranged in one of the conducting elements 204. The embodiment of the neural prosthesis 200 of FIG. 2 shows that the conducting elements 204 and the coupling elements 206 have the same diameters or dimensions in a transverse direction.

In a modified embodiment, the conducting elements 204 and the coupling elements 206 can also be equal with respect to their dimensions.

Figure 3:
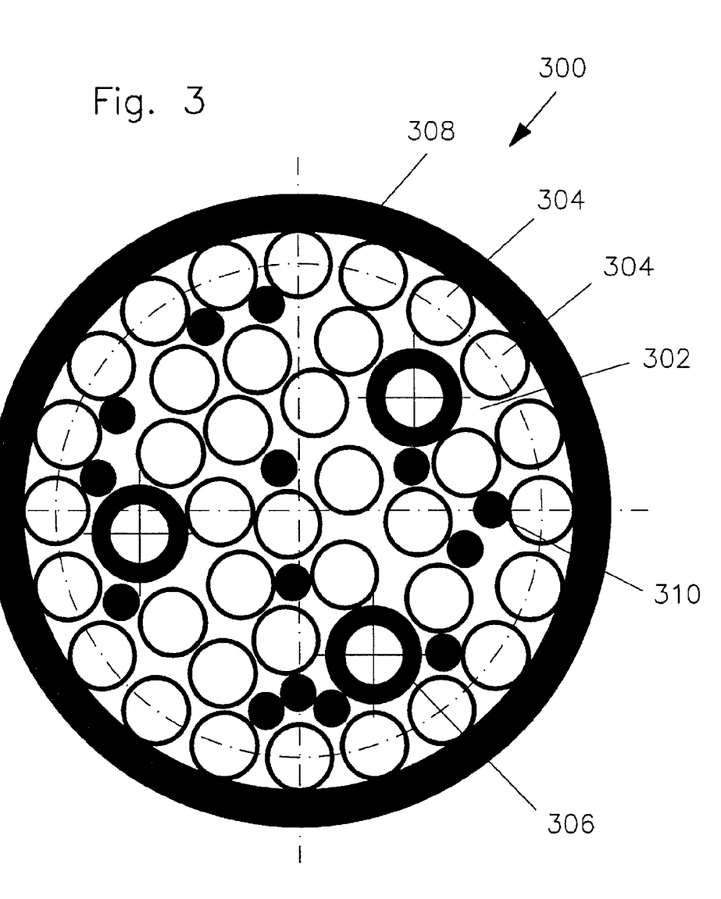
FIG. 3: a further schematic representation of a portion of a neural prosthesis in section along a transverse direction.

FIG. 3 shows a further schematic representation of a portion of a neural prosthesis 300 in section along a transverse direction, which comprises a multitude of conducting elements 304, 310, three coupling elements 306, and a jacket 308.

The neural prosthesis 100 and the neural prosthesis 300 can be identical, the conducting elements 104 and the conducting elements 304 can be identical, the coupling elements 106, 106' and the coupling elements 306 can be identical, and the jacket 108 and the jacket 308 can be identical.

The conducting elements 304 of the coupling element receptacle 302 have a tubular shape, whereas the conducting elements 310 of the coupling element receptacle 302 have a rod shape. In particular, the rod-shaped conducting elements 310 can be formed as stabilizing elements, which provide sufficient stiffness or stability of the neural prosthesis 300 against outside influences, whereas the conducting elements 304 are rather flexible and bendable, so that tissue surrounding a neural prosthesis is not squeezed or damaged when a neural prosthesis was inserted into a body region to be treated.

As can be seen in FIG. 3, the coupling elements 306 have larger dimensions than the tubular conducting elements 304.

In a modified embodiment, the coupling elements are formed similarly or analogously to the rod-shaped conducting elements 310 shown in FIG. 3. With such a configuration, a coupling element does not have a passage or fluid channel. Here, a fluid exchange (such as blood, hormones, etc.) takes place or is performed only via the conducting elements surrounding the coupling element. Moreover, in a further modified configuration, the stabilizing elements can be formed like the coupling elements 306 shown in FIG. 3. Such a hollow-cylindrical configuration can achieve a higher bending strength of a stabilizing element compared to a rod-shaped stabilizing element, while the weight and the displacement volume are less increased than with a full-cylindrical configuration.

Figure 4:
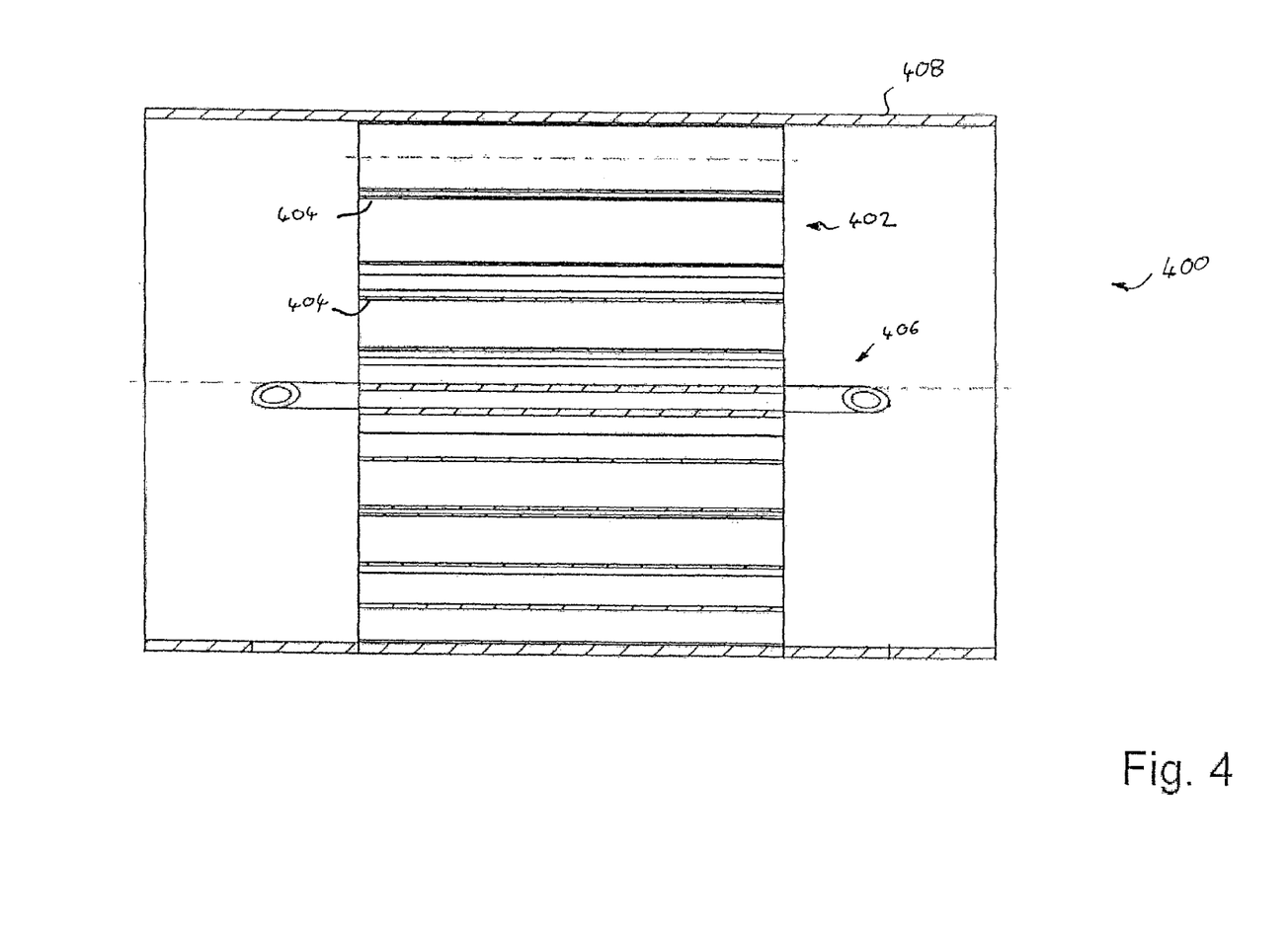
FIG. 4: a schematic representation of a neural prosthesis in section along a longitudinal direction.

FIG. 4 shows a schematic representation of a neural prosthesis 400 in section along a longitudinal direction, which comprises a coupling element receptacle 402 with a multitude of conducting elements 404, a coupling element 406, and a jacket 408.

The neural prosthesis 100 and the neural prosthesis 400 can be identical, the coupling element receptacle 102 and the coupling element receptacle 402 can be identical, the conducting elements 104 and the conducting elements 404 can be identical, the coupling elements 106, 106' and the coupling elements 406 can be identical, and the jacket 108 and the jacket 408 can be identical.

For example, a surgical suture (not shown) can be passed through at least one of the conducting elements 404. Moreover, several surgical sutures can be passed through one or different conducting elements 404, which after the arrangement of the neural prosthesis 400 at a nerve area allows a fixation of the nerve area by means of the surgical suture or by means of the surgical sutures. Fixation can be accomplished by wrapping the nerve area with the suture or by sewing the nerve area on.

Figure 5:
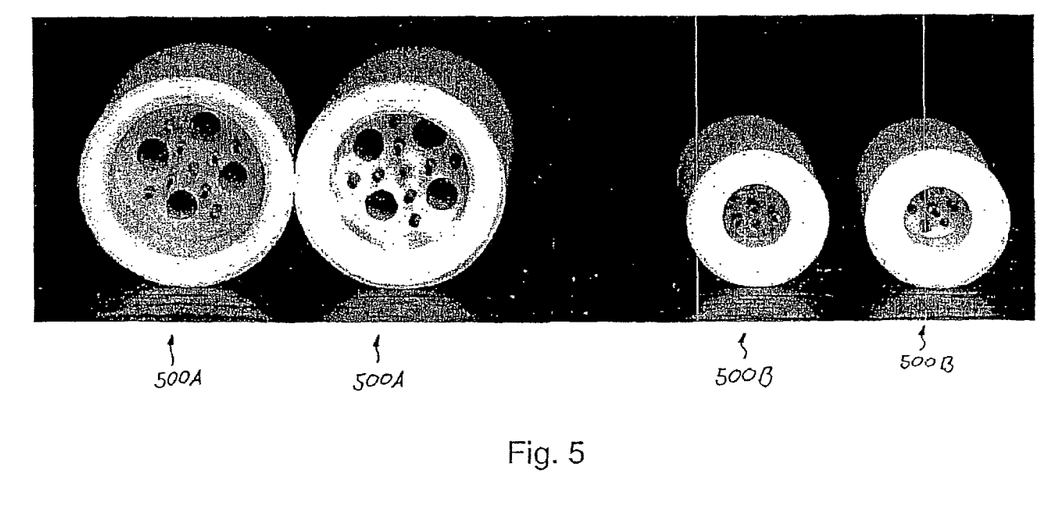
FIG. 5: a perspective representation of a further configuration of a neural prosthesis, FIG. 6 a schematic representation of an configuration of a coupling element receptacle in top view and in side view.

FIG. 5 shows a perspective representation of a neural prosthesis 500A and a neural prosthesis 500B.

The neural prostheses 500A and 500B are each configured as integral elements. Instead of a plurality of conducting elements, the neural prostheses 500A and 500B each have several channels. It is particularly obvious that coupling elements are arranged at least in some channels.

In addition to channels that comprise coupling elements, the neural prosthesis 500A comprises additional channels having comparatively larger dimensions in order to facilitate or promote growing through of tissue.

As shown, in particular coupling element receptacles of the neural prostheses 500A and 500B are configured integrally. Moreover, a jacket can be formed integrally with a coupling element receptacle.

In a modified configuration of a neural prosthesis 500A and 500B, the neural prosthesis does not have a jacket. For example, a jacket can be omitted if a stability of the neural prosthesis sufficient for the application case is ensured by an integral configuration of the coupling element receptacle.

Figure 6:
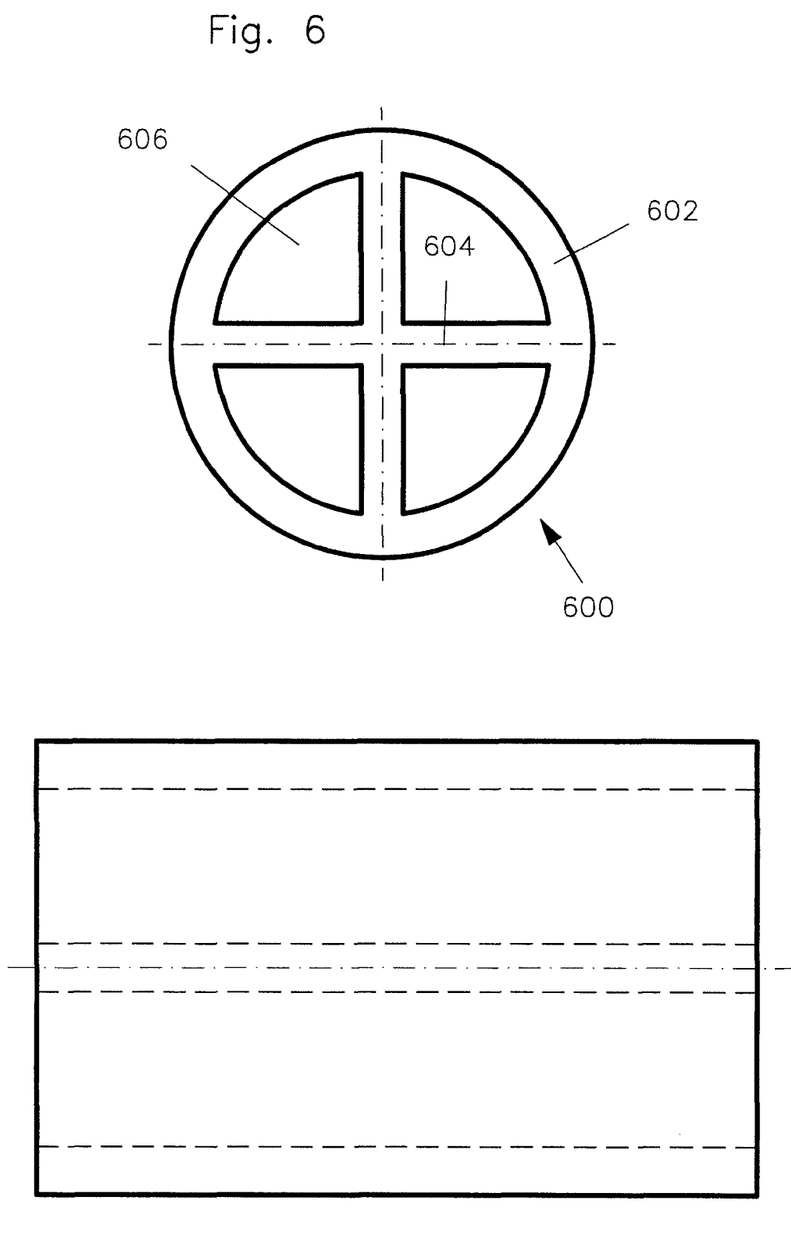

FIG. 6 shows a schematic representation of a configuration of a coupling element receptacle 600 in top view, wherein coupling elements are arrangeable in a circumferential area 602 and/or in an area of the connecting struts 604 or in intermediate areas 606.

Moreover, FIG. 6 shows a schematic representation of a configuration of the coupling element 600 in side view.

The neural prostheses 100, 200, 300, 400, 500 shown in FIGS. 1 through 5 can each be neural prostheses, wherein the jacket and the coupling element receptacle comprise resorbing material, so that the neural prosthesis is substantially absorbed after an absorption time.

Furthermore, the neural prostheses 100, 200, 300, 400, 500 can comprise gelatin and/or polyglycolic acid as the resorbing material.

At least one of the coupling elements of the described neural prostheses 100, 200, 300, 400, 500 can be made of non-resorbable material. In particular, the non-resorbable material can be a metal. Preferably, the metal is titanium, surgical steel or a material used in the medical field.

Moreover, the neural prostheses 100, 200, 300, 400, 500 comprise at least one biochemical stimulator to stimulate coupling of two nerve areas, wherein the at least one stimulator is arranged in one or more conducting elements and/or channels and/or at least one coupling element.

If nerves are injured or completely severed, nerve signals are partially or fully interrupted, which as a further result causes a degeneration of the affected nerves and consequently affects strongly the normal activity of the affected living being. With the help of the neural prostheses 100 to 500, nerve regeneration is to be improved and muscular atrophy prevented, the body's own reparation processes accelerated, and the signal transmission via the injured nerve region fully restored.

Advantageously, the neural prostheses 100, 200, 300, 400, 500 are formed as adaptive neural prostheses and can restore a direct connection between the present severed parts of a nerve or nerve fiber after being inserted between to nerve areas. Thus, neural prostheses of the type described allow a targeted growing together of a severed nerve tract or nerve, for example by introducing nerve ends or nerve areas into a neural prosthesis, which as a result grow together again. Advantageously, the nerve signals that are transmitted via a neural prosthesis can thereby innervate a peripheral portion of a nerve or tissue, promote the regeneration, and prevent atrophic degeneration of an effector organ (such as the muscular system).

In particular, the coupling element receptacles of the type described can be provided with a specific number of more or less large conducting elements, which are formed as tubes. Preferably, coupling element receptacles comprise a larger number of different conducting elements or microtubes, which are adhered to each other by means of an adhesive.

Advantageously, neural prostheses of the type described are substantially resorbable.

An absorption time can be independent of ambient conditions in a body to be treated. For example, depending on blood flow conditions, the absorption may take up to nine months. Absorption substantially takes place by hydrolysis without residual materials being left. Hereby, in particular the formation of reactive fibroses, which may negatively influence the functioning of the regenerating nerves, can be prevented. By a corresponding resorbing material of a neural prosthesis, the absorption time can be adjusted to a corresponding body region.

Coupling element receptacles of the type described can additionally comprise caverns filled with liquids, gels, or solid material, which include stimuli to stimulate growing together of severed nerves via biochemical reactions.

Furthermore, neural prostheses of the type described can comprise additionally comprise mechanical and/or electrical stimulators, which can be arranged on a neural prosthesis or coupled thereto. Preferably, mechanical and/or electrical stimulators contact the nerve areas to be treated.

| List of Reference Numerals | |
|---|---|
| 100 | neural prosthesis |
| 102 | coupling element receptacle |
| 104 | conducting element |
| 106, 106' | coupling elements |
| 106A, 106B | coupling portions |
| 108 | jacket |
| 110 | passage 110 of a coupling element |
| 112, 114 | ends of a coupling element |
| 116, 118 | contact area |
| 120, 122 | adaptation area |
| KA | coupling axis |
| 200, 300, 400, 500A, 500B | neural prosthesis |
| 202, 302, 402 | coupling element receptacle |
| 204, 304, 404 | conducting element |
| 206, 306, 406 | coupling element |
| 208, 308, 408 | jacket |
| 310 | rod-shaped conducting element |
| 600 | coupling element receptacle |
| 602 | circumferential area |
| 604 | connecting struts |
| 606 | intermediate areas |

The invention claimed is:

1. A neural prosthesis, comprising:
a coupling element receptacle, and
at least one coupling element having a first coupling portion and a second coupling portion,
the at least one coupling element being made of non-resorbable material comprising at least one of titanium or surgical steels,
the at least one coupling element being bonded to the coupling element receptacle,
the first coupling portion being arrangeable at a first nerve area and the second coupling portion being arrangeable at a second nerve area, so that the first nerve area and the second nerve area are coupleable by means of the neural prosthesis,
the coupling element receptacle including a plurality of rod-shaped and/or tubular conducting elements having ends arrangeable between or in contact with a first nerve end and a second nerve end,
the plurality of rod-shaped and/or tubular conducting elements being non-concentric to each other and being parallel to each other,
the at least one coupling element being arranged in the coupling element receptacle, and
the first coupling portion and the second coupling portion projecting beyond a first contact area and a second contact area of the coupling element receptacle, respectively.

2. The neural prosthesis according to claim 1, where the first coupling portion and the second coupling portion project about 0.1 μm to about 8 mm or about 5 mm to 3 cm out from the first contact area and the second contact area of the coupling element receptacle, respectively.

3. The neural prosthesis according to claim 1, where the at least one coupling element is hollow.

4. The neural prosthesis according to claim 1, further comprising a jacket,
where the coupling element receptacle and at least partly the at least one coupling element are arranged within the jacket.

5. The neural prosthesis according to claim 4, where the jacket is substantially a hollow cylinder,
where the jacket projects beyond the first contact area and the second contact area of the coupling element receptacle by about 0.1 μm to about 8 mm or about 2 mm to about 15 mm.

6. The neural prosthesis according to claim 4, where areas of the jacket surround the first contact area and the second contact area of the coupling element receptacle and the areas respectively define a first adaptation area and a second adaptation area,
where the first adaptation area and the second adaptation area each has a width of about 0.5 μm to about 2.8 mm, or from about 2.5 mm to about 10 mm, or from about 2.3 mm to about 15 mm.

7. The neural prosthesis according to claim 4, where the jacket and the coupling element receptacle comprise resorbing material, so that the neural prosthesis is substantially absorbed after an absorption time.

8. The neural prosthesis according to claim 7, where the resorbing material is gelatin and/or polyglycolic acid.

9. The neural prosthesis according to claim 1, where the neural prosthesis comprises three or more coupling elements.

10. The neural prosthesis according to claim 1, comprising at least one biochemical stimulator,
where the biochemical stimulator is adapted to stimulate coupling of the first nerve area and the second nerve area, and
the at least one biochemical stimulator is arranged in one or more of the plurality of rod-shaped and/or tubular conducting elements and/or in one or more channels and/or in the at least one coupling element.

11. The neural prosthesis according to claim 1, where a surgical suture is arranged in the coupling element receptacle,
the surgical suture being different than the coupling element.

12. The neural prosthesis according to claim 1, where the first nerve area is the first nerve end, and
where the second nerve area is the second nerve end,
the first nerve end being a first severed surface of a nerve and the second nerve end being a second severed surface of the nerve.

13. The neural prosthesis according to claim 1, where the plurality of rod-shaped and/or tubular conducting elements are different than the at least one coupling element.

14. The neural prosthesis according to claim 1, where the first contact area is formed by first ends of the plurality of rod-shaped and/or tubular conducting elements, and the second contact area is formed by second ends of the plurality of rod-shaped and/or tubular conducting elements.

15. The neural prosthesis according to claim 1, where ends of the first coupling portion and the second coupling portion are acute.

16. The neural prosthesis according to claim 1, where the neural prosthesis is comprised of a resorbing material, so that only the at least one coupling element, made of the non-resorbable material comprising at least one of titanium or surgical steels, remains after an absorption time.

17. A neural prosthesis for use in a treatment of severed nerves, the neural prosthesis comprising:
a coupling element receptacle, and
at least one coupling element having a first coupling portion and a second coupling portion,
the at least one coupling element being made of non-resorbable material comprising at least one of titanium or surgical steels,
the at least one coupling element being bonded to the coupling element receptacle,
the first coupling portion being arrangeable at a first nerve area of a severed nerve and the second coupling portion being arrangeable at a second nerve area of the severed nerve, so that the first nerve area and the second nerve area are coupleable by means of the neural prosthesis,
the coupling element receptacle including a plurality of rod-shaped and/or tubular conducting elements having ends arrangeable between or in contact with a first nerve end of the severed nerve and a second nerve end of the severed nerve,
the plurality of rod-shaped and/or tubular conducting elements being non-concentric to each other and being parallel to each other,
the at least one coupling element being arranged in the coupling element receptacle, and
the first coupling portion and the second coupling portion projecting beyond a first contact area and a second contact area of the coupling element receptacle, respectively.

18. The neural prosthesis according to claim 17, where the plurality of rod-shaped and/or tubular conducting elements are different than the at least one coupling element.

19. The neural prosthesis according to claim 17, where the first contact area is formed by first ends of the plurality of rod-shaped and/or tubular conducting elements, and the second contact area is formed by second ends of the plurality of rod-shaped and/or tubular conducting elements.

\* \* \* \* \*